United States Patent [19]

Tabata

[11] Patent Number: 4,519,397
[45] Date of Patent: May 28, 1985

[54] PULSE DETECTOR
[75] Inventor: Junichi Tabata, Tokyo, Japan
[73] Assignee: Kabushiki Kaisha Daini Seikosha, Tokyo, Fed. Rep. of Germany
[21] Appl. No.: 403,427
[22] Filed: Jul. 30, 1982
[30] Foreign Application Priority Data
Aug. 26, 1981 [JP] Japan .................. 56-133573
[51] Int. Cl.³ .............................. A61B 5/02
[52] U.S. Cl. .................................. 128/706
[58] Field of Search ............... 128/695, 696, 700, 702, 128/703, 704, 706, 902; 328/112, 120, 163, 169; 307/543, 566

[56] References Cited
U.S. PATENT DOCUMENTS 3,927,377 12/1975 Iwazumi .................. 128/708 X
3,934,577 1/1976 Romani ...................... 128/661
4,000,461 12/1976 Barber et al. ............... 128/708
4,085,340 4/1978 Salesky ....................... 328/169
4,181,134 1/1980 Mason ........................ 128/706
4,261,369 4/1981 Allor ......................... 128/696

Primary Examiner—Kyle L. Howell
Assistant Examiner—Francis J. Jaworski
Attorney, Agent, or Firm—Robert E. Burns; Emmanuel J. Lobato; Bruce L. Adams

[57] ABSTRACT

A pulse detector comprising an electrocardiac potential detector for detecting an electrocardiac signal induced to the skin of the person and a pulse counter for counting the pulse rate. The pulse detector comprises a pulse detection supervisory system for automatically controlling a pulse detection sensitivity and noise sensitivity at the optimum value.

9 Claims, 4 Drawing Figures

PULSE DETECTOR

BACKGROUND OF THE INVENTION

The present invention relates to a pulse detector, and more particularly to a pulse detector comprising a pulse counter and an electrocardiac potential detector for detecting an electrocardiac potential induced on the skin of a person and for counting the pulse rate.

Generally the electrocardiac potential induced between both arms of a person consists of P wave, Q-R-S wave and T wave which develop periodically. Of these the variation in the electric potential $V_{p-p}$ of the Q-R-S wave is largest, i.e., between about 0.2 mV and 1.0 mV. Thus the method of detecting the Q-R-S wave is generally applied. Further, the electric noise at 50 Hz or 60 Hz induded on the skin of the person from the outside overlaps the electrocardiac potential. In counting the pulses, accordingly, it is necessary to eliminate a large noise level for accurately sensing minute signals.

A conventional circuit system for counting the pulses by detecting the electrocardiac potential is shown in a circuit block of FIG. 2. An electrocardiac potential sensing electrode 1 is connected to an input terminal of an amplifier 2. Faint electrocardiac potentials are amplified by the amplifier 2.

An output signal of the amplifier 2 is fed to a band-pass filter 3. A center frequency $f_0$ of the band-pass filter 3 is designed at the frequency of the Q-R-S wave, about 20 Hz; while the P-wave and T-wave, and the 50 Hz and 60 Hz noises are attenuated or eliminated. An output signal of the band-pass filter 3 is fed to a low-pass filter 4. The noise, which is not eliminated by the band-pass filter 3 but transmitted to the low-pass filter 4, is eliminated by the low-pass filter 4. An output signal of the low-pass filter 4 is fed to a comparator 5. The comparator 5 detects only the Q-R-S wave of more than a given electric potential level and produces a pulse signal at an output terminal. The output signal of the comparator 5 is fed to a counter 6. The counter 6 counts the interval T (second) between the pulse signals and performs the operation of 60/T, and produces the operated result. The operated result indicates the pulse rate of the person. The output of the counter 6 is fed to a display 7. Thus the pulse rate is displayed on the display such as liquid crystal through a driver.

The electrocardiac potentials of persons differ according to their physical constitution and age. The induced electrocardiac potentials as well as noises differ even in the same person at different times because of the difference in a circumstances, such as humidity. Accordingly, the conventional type counter is disadvantageous in that the counting may sometimes stop by change of the person or even by change of the circumstances, and misoperation may easily occur by noise. Conventionally, a method of detecting even a small electrocardiac potential has been tried, in which the amplification degree of the amplifier 2 and the sensitivity of the comparator 5 are set at a high level on the assumption that these phenomena would occur. However, the pulse could not always be detected.

SUMMARY OF THE INVENTION

It is an object of the present invention to provide a pulse detector comprising a pulse counter, an electrocardiac potential detector, a pulse detection supervisory system and a detection sensitivity regulation system.

It is another object of the invention to provide a pulse detector capable of counting the pulses at high accuracy for any person under any circumstances.

It is another object of the invention to provide a pulse detector having a pulse detection supervisory system for automatically controlling a pulse detection sensitivity and noise sensitivity at the optimum value.

Hereinafter the present invention will be illustrated in conjunction with the accompanied drawings.

DESCRIPTION OF THE PREFERRED EMBODIMENTS

Figure 1:
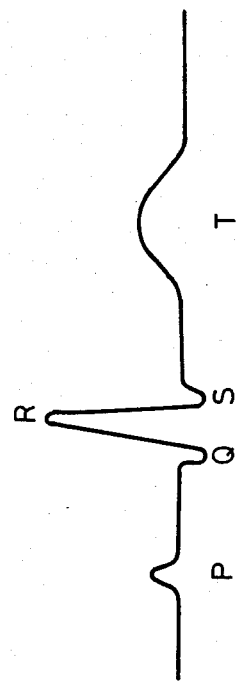
FIG. 1 is a schematic view of the electrocardiac potential waveform induced at both arms of the person.
Figure 2:
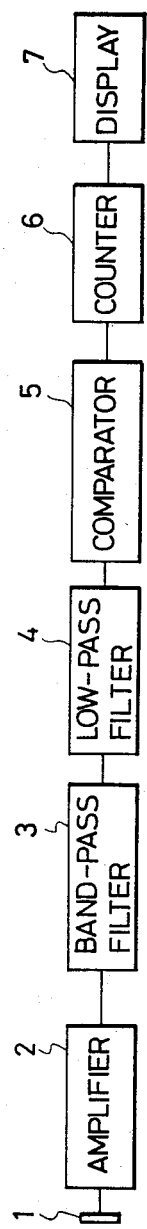
FIG. 2 is a block diagram of the conventional pulse detector.
Figure 3:
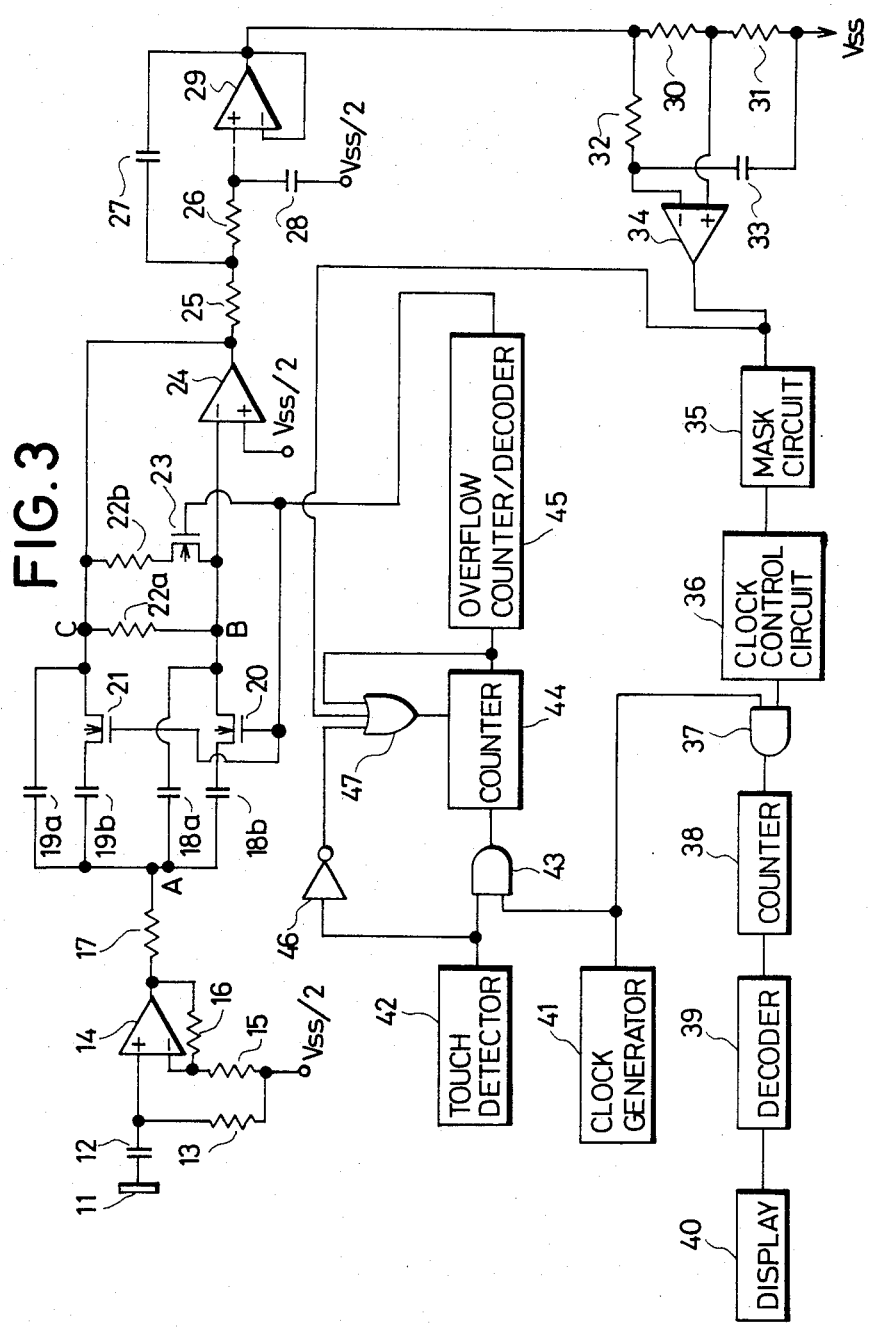
FIG. 3 is a circuit diagram of one embodiment of the pulse detector according to the present invention.

FIG. 3 shows a pulse detector according to the present invention.

In the figure, reference numeral 11 denotes an electrocardiac potential sensing electrode. A pulse is counted by contacting a part of the body surface, e.g. a part of the skin of one arm, to the earth or ground of the circuit and a part of the skin of the other arm, e.g. the finger tip, to the electrocardiac sensing electrode 11.

The electrocardiac potential sensing electrode 11 is connected to a middle point electric potential of the source voltage via a condenser 12 and a resistor 13. In the pulse detector according to the present invention, the plus electric potential of the power source serves as an earth or ground and the minus electric potential of the same serves as $V_{ss}$. Thus the middle point electric potential is $V_{ss}/2$.

The condenser 12 eliminates the DC component of the signal and the resistor 13 discharges the electric charges of the condenser 12. A connecting point between the condenser 12 and the resistor 13 is connected to a plus input terminal of an OP amplifier 14. An output terminal of the OP amplifier 14 is connected to the $V_{ss}/2$ via resistors 15 and 16. A minus input terminal of the OP amplifier 14 is connected to a connecting point between the resistors 15 and 16. An electrocardiac potential amplifier consists of the OP amplifier 14, and the resistors 15 and 16. The output terminal of the OP amplifier 14 is connected to a resistor 17 and the other terminal of the resistor 17 is connected to a point A in the circuit diagram.

A condenser 18a is connected to points A and B in the figure. One terminal of a condenser 18b is connected to point A and the other terminal of the same is connected to point B via a MOSFET 20. A condenser 19a is connected to points A and C. One terminal of a condenser 19b is connected to point A and the other terminal of the same is connected to point C via a MOSFET 21.

A resistor 22a is connected between points B and C. One terminal of a resistor 22b is connected to point C and the other terminal of the same is connected to point B via a MOSFET 23. A minus input terminal of an OP amplifier 24 is connected to point B and a plus input terminal of the same is connected to $V_{ss}/2$, and an output terminal of the same is connected to point C. Gate terminals of the MOSFETs 20, 21 and 23 are connected to an output terminal of an overflow cycle counter/decoder 45.

A band-pass filter (B.P.F.) is made up of the resistors 17 and 22a, the condenser 19a and the OP amplifier 24. A pulse and noise sensitivity regulating circuit is made up of the condensers 18b and 19b, the resistor 22b, and the switching MOSFETs 20, 21 and 23.

An output terminal of the OP amplifier 24 is connected to a plus input terminal of an OP amplifier 29 via series resistors 25 and 26. A connecting point between the resistors 25 and 26 is connected to an output terminal of the OP amplifier 29 via a condenser 27. A condenser 28 is connected to a plus input terminal of the OP amplifier 29 and $V_{ss}/2$. A minus input terminal of the OP amplifier 29 is connected to the output terminal.

A secondary low-pass filter is made up of the resistors 25 and 26, the condensers 27 and 28, and the OP amplifier 29.

The output terminal of the OP amplifier 29 is connected to $V_{ss}$ via series resistors 30 and 31. A connecting point between the resistors 30 and 31 is connected to a plus input terminal of an OP amplifier 34. A resistor 32 is connected between a minus input terminal of the OP amplifier 34 and the output terminal of the OP amplifier 29. A condenser 33 is connected between the minus input terminal of the OP between the minus input terminal of the OP amplifier 34 and the $V_{ss}$.

A voltage comparator is made up of the resistors 30, 31 and 32, the condenser 33 and the OP amplifier 34.

A pulse detector is composed of the above circuit blocks. The operation of the pulse detector is omitted since it operates in a similar manner to the conventional circuit blocks.

The OP amplifier 34 at the final stage of the above circuit structure produces a pulse only when it detects the Q-R-S wave of the electrocardiac potential. Accordingly, the output signal of the OP amplifier 34 is at a logic level "0" except when operating in the pulse detection mode or in case the electrocardiac potential signal is too small to be detected even though the OP amplifier is in the pulse detection mode. The output signal of the OP amplifier 34 is fed to a mask circuit 35. The mask circuit 35 sets a mask period in which no input signals are received for a given period after the Q-R-S wave is detected. The mask period is provided to prevent a misdetection of a T-wave with comparatively high amplitude and the T-wave occurs about 300 msec. after the Q-R-S wave in the normal electrocardiac potential waveform. An output terminal of the mask circuit 35 is connected to an input terminal of a clock control circuit 36. When an output signal of the mask circuit 35 changes to a logic level "1", an output signal of the clock control circuit 36 changes to a logic level "1" synchronism with the former output signal. The output signal of the mask circuit 35 maintains "1" for a given period, and then becomes "0". Then the Q-R-S wave is fed to the mask circuit 35, and detected by the pulse detector, and the output signal of the mask circuit 35 is "1" again. The output signal of the clock control circuit 36 keeps "1" while the output signal of the mask circuit 35 changes from "1" to "0" and then "1".

The output terminal of the clock control circuit 36 is connected to one input terminal of a 2-input AND circuit 37. An output terminal of a clock generator 41 is connected to other input terminal of the 2-input AND circuit 37.

While the output signal of the clock control circuit 36 is "1", which corresponds to the period of the Q-R-S wave, a clock signal is fed to a counter 38 via the AND circuit 37. An output terminal of the counter 38 is connected to an input terminal of a decoder 39, and an output terminal of the decoder 39 is connected to a display 40. The circuit blocks 35–39 comprise signal processing circuitry for processing the output detection signals from the voltage comparator and applying corresponding drive signals to the display 40 to cause the display 40 to display the pulse rate.

Hereinafter the manner of counting the pulse rate by the above circuit structure will be illustrated.

The number of clock pulses fed to the counter 38 during the period corresponding to the period of the Q-R-S wave is changed into the following formula and decoded into the pulse rate.

$$\text{the pulse rate} = \frac{60(\text{sec})}{\text{pulse period (sec)}} = \frac{60(\text{sec})}{1/f \times \text{the count number}}$$

where f is the clock frequency.

When the clock signal frequency is 256 Hz and the count number is 200, for instance, $$\text{the pulse rate} = \frac{60}{1/256 \times 200} \approx 77$$

is decoded and displayed. The pulse is detected and displayed by the above circuit system.

Further, the present invention comprises a pulse detection supervisory system and a detection sensitivity regulation system which prevents the inability of detection caused by dispersion in the electrocardiac potential of the person or a change in the circumstances, or the misoperation by noise.

These systems will now be illustrated.

An output terminal of a touch detector 42 is connected to one input terminal of a 2-input AND circuit 43, and the other input terminal of the same is connected to an output terminal of the clock generator 41. An output terminal of the 2-input AND circuit 43 is connected to an input terminal of a counter 44. An output terminal of the counter 44 is connected to an input terminal of an overflow counter/decoder 45 and one input terminal of a 3-input NOR circuit 47. An input terminal of an inverter 46 is connected to the output terminal of the touch detector 42, and an output terminal of the same is connected to another input terminal of the 3-input NOR circuit 47. The third input terminal of the 3-input NOR circuit 47 is connected to the output terminal of the OP amplifier 34 which is the last stage of the pulse detector. An output terminal of the 3-input NOR circuit 47 is connected to a reset terminal of the counter 44. An output terminal of the overflow counter/decoder 45 is connected to gates of the MOSFETs 20, 21 and 23. The circuitry including the clock generator 41, AND circuit 43, counter 44, overflow counter/decoder 45, inverter 46 and NOR circuit 47 comprise timing means for developing an output signal which is applied to the gates of the MOSFETs 20, 21 and 23 after the elapse of a preselected time T (as described hereinbelow) to change the parameters of the filter in the event no electrocardiac signal is detected within the preselected time period T. The touch detector 42 comprises enabling means for enabling the timing means when the pulse detector is placed in the pulse counting mode.

Now the operation of the pulse detection supervisory system and the detection sensitivity regulation system will be illustrated.

When the person touches his finger tip to the electrocardiac potential sensing electrode 11, the touch detector detects the pulse counting mode and produces an output enabling signal at a logic level "1". This enables the timing means and a clock signal from the clock generator 41 is fed to the counter 44 through the AND circuit 43. The counter 44 produces a carry signal at the output terminal when the count number exceeds a given number. The preselected given count number corresponds to the time T which is the pulse period of the usually anticipated minimum pulse rate (i.e. in case the pulse period is maximum) plus the delay time of the signal in the detector. Thus the given count number $= T \times f$
where f is the clock frequency.

Accordingly, the counter 44 produces the carry signal when the pulse detector cannot detect a signal even in the pulse counting mode. Because, when the electrocardiac signal is detected, the carry signal is not produced since the counter 44 is reset by the output signal from the OP amplifier 34. In a non-pulse counting mode, the counter 44 is reset by the touch detector 42. While in a pulse counting mode, the counter 44 is reset by the carry signal as soon as it produces the carry signal and the counter starts to count the clock pulses again. When the counter 44 produces the carry signal, the overflow counter/decoder 45 counts and decodes the carry signal and produces the result. As a consequence the MOSFETs 20, 21, 23 are turned on and the BPF parameters or characteristics are changed. It is to be noted that in changing the BPF characteristics, an increase in the gain at the center frequency (in this case the Q-R-S wave frequency) causes the gain of the noise (especially induction noise at 50 Hz or 60 Hz) to increase. This phenomenon is not preferable since misoperation easily occurs due to such noise. It is therefore necessary to increase the Q-value of the filters as well as to increase the gain of the center frequency. This is achieved in the BPF of the type in FIG. 3 by decreasing the value of the resistor 22a and increasing the value of the condensers 19a and 18a.

When the MOSFETs 20, 21 and 23 are turned on, the sensitivity for detecting the electrocardiac signal is improved, and the sensitivity for detecting noise is kept as it is or decreased.

Although the two switching condensers, one resistor and three MOS transistors are shown in FIG. 3 to avoid complication of the figure, additional ones of these circuit element can be provided to enable the regulation of sensitivity in an even wider range.

Figure 4:
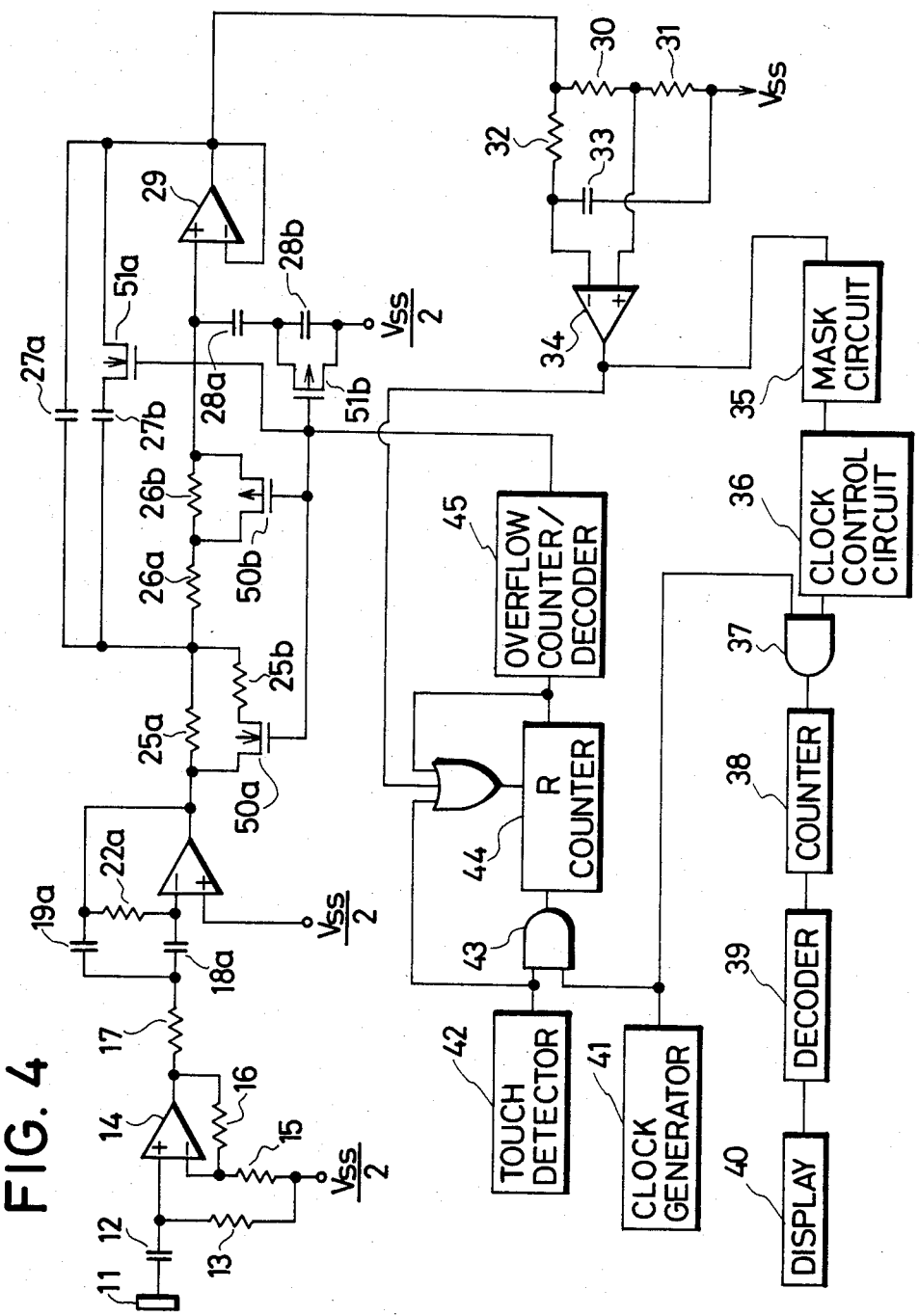
FIG. 4 is another embodiment of the pulse detector according to the present invention.

FIG. 4 shows another embodiment of the present invention. The pulse detection sensitivity and the noise sensitivity are automatically regulated by controlling the gain at the center frequency and the Q-value of the low-pass filter. Thus the circuit structure is similar to FIG. 3 except for the low-pass filter portion. Since the circuit constant of the band-pass filter is not controlled in the embodiment of FIG. 4, the MOSFETs 20, 21, 23, condensers 18b and 19b and the resistor 22b shown in FIG. 3 are not needed. Like parts in FIGS. 3 and 4 have been designated by the same reference numerals and the description thereof is eliminated.

The operation of FIG. 4 will now be illustrated. Before the pulse detection, the output signal of the touch detector 42 is at "0" level and the timing means is in the non-enabled state. The outputs from the counter 44 and the overflow counter/decoder 45 are therefore at "0" level. Thus N channel MOSFETs 50a and 51a are in a non-conductive state and P channel MOSFETs 50b and 51b are in a conductive state. As a result the gain at the center frequency and the Q value of the low-pass filter are decided by resistors 25a, 26a and condensers 27a and 28a.

Now the pulse counting mode will be illustrated. When the pulse counter is placed in a pulse counting state by contacting the skin of the person to the sensing electrode 11, the output signal of the touch detector changes to a "1" level, thereby placing the timing means in the enabled state, and the counter 44 starts counting the clock pulses produced from the clock generator 41. If the sensitivity of the pulse detector for detecting the electrocardiac signal is sufficient, the comparator 34 produces the pulse signal corresponding to the electrocardiac potential signal (i.e. the pulse). The counter 44 is reset by the pulse signal and it starts to count the clock pulses. In case the sensitivity of the pulse detector for detecting the electrocardiac signal is insufficient, the comparator 34 does not produce the output signal although the maximum count time of the counter 44 is over. So the counter 44 produces the carry signal, and the overflow counter/decoder 45 counts the signal and produces the decoded information. Simultaneously the counter 44 is reset by the carry signal, and it starts counting the clock pulses.

The output signal of the overflow counter/decoder 45 changes to the logic level "1". Then the N channel MOSFETs 50a and 51a switch to a conductive state and P channel MOSFETs 50b and 51b are in a non-conductive state. As the result, the gain at the center frequency and the Q value of the low-pass filter are decided by a parallel combined resistance combination consisting of the resistors 25a and 25b, a series resistance combination consisting of the resistors 26a and 26b, a parallel condenser combination consisting of the condensers 27a and 27b, and a series condenser combination consisting of the condensers 28a and 28b. At this time, the center frequency does not change and the gain and Q value increase in the electric characteristics of the low-pass filter. Although only the two switching condensers and the two resistors are shown in FIG. 4 to avoid the complication of the figure, additional ones can be provided to enable the regulation of sensitivity over an even wider range.

As illustrated, the pulse detection supervisory system and the detection sensitivity regulation system are provided within the pulse counting system according to the present invention, whereby the dispersion of the electrocardiac signal over a wide range of persons or the inability of pulse counting caused by a change in the circumstances can be detected, and the pulse detecting sensitivity is automatically increased and also the increase in the noise sensitivity is prevented. As a result the inability of counting caused by the change of the person is avoided and a pulse counter with sufficient counting capacity against the change in the circumstances can be provided.

What I claim is:

1. In a pulse detector of the type having a pulse detecting portion having an electrocardiac potential sensing electrode for sensing electrocardiac potentials, an amplifier for amplifying electrocardiac potential signals derived from said electrocardiac potential sensing electrode, a filter for eliminating noise and being connected to said amplifier, and a voltage comparator for detecting electrocardiac potentials higher than a predetermined potential level and producing corresponding output signals; a signal processing circuit connected to said voltage comparator for processing the output signals and producing processed output signals; and a display responsive to the processed output signals for indicating a pulse rate; the improvement comprising timer means connected to said voltage comparator and operable when enabled to effect a change of the filter characteristics of said filter if an electrocardiac potential higher than said predetermined potential level is not detected within a preselected given time, said timer means including a clock generator for producing a clock signal, and a counter for counting said clock signal and having a reset terminal connected to receive the output signals from said voltage comparator; and enabling means for enabling said timer means.

2. A pulse detector as claimed in claim 1; wherein said enabling means comprises a touch detector for making contact with a human body.

3. In a pulse detector for detecting electrocardiac potentials indicative of the pulse rate of a person's heart: pulse detecting means for detecting electrocardiac signal potentials from the skin surface of a person which are indicative of the person's pulse rate and producing corresponding output detection signals when the detected electrocardiac signal potentials are higher than a predetermined potential level, the pulse detecting means including adjustable filtering means having adjustably settable filter characteristics for filtering unwanted electrical noise from the detected electrocardiac signal potentials; and timing means for detecting when the time between successive groups of output detection signals exceeds a preselected given time and for effecting adjustment of the filter characteristics of the filtering means in response to such detection, the timing means comprising a clock generator for generating clock pulses, a resettable counter for counting the clock pulses, and means for effecting adjustment of the filter characteristics of the filtering means when the count content of the counter exceeds a predetermined value and the time between successive groups of output detection signals exceeds said preselected given time.

4. A pulse detector according to claim 3; including enabling means for enabling the timing means.

5. A pulse detector according to claim 8; wherein the enabling means comprises a touch detector for making contact with the person.

6. A pulse detector according to claim 3; wherein the successive groups of output detection signals comprise successive ones of the output detection signals.

7. In a pulse detector for detecting electrocardiac potentials indicative of the pulse rate of a person's heart: pulse detecting means for detecting electrocardiac signal potentials from the skin surface of a person which are indicative of the person's pulse rate and producing corresponding output detection signals when the detected electrocardiac signal potentials are higher than a predetermined potential level, the pulse detecting means including adjustable filtering means having adjustably settable filter characteristics for filtering unwanted electrical noise from the detected electrocardiac signal potentials; and timing means for detecting when the time between successive groups of output detection signals exceeds a preselected given time and for effecting adjustment of the filter characteristics of the filtering means in response to such detection, the successive groups of output detection signals comprising successive ones of the output detection signals.

8. In a pulse detector for detecting electrocardiac potentials indicative of the pulse rate of a person's heart: pulse detecting means for detecting electrocardiac signal potentials from the skin surface of a person which are indicative of the person's pulse rate and producing corresponding output detection signals when the detected electrocardiac signal potentials are higher than a predetermined potential level, the pulse detecting means comprising adjustable filtering means having adjustably settable filter characteristics for filtering unwanted electrical noise from the detected electrocardiac signal potentials, a voltage comparator for detecting electrocardiac signal potentials higher than said predetermined potential level and for producing at an output terminal thereof the corresponding output detection signals; and timing means for detecting when the time between successive groups of output detection signals exceeds a preselected given time and for effecting adjustment of the filter characteristics of the filtering means in response to such detection, the timing means including a clock generator for generating clock pulses, and a resettable counter for counting the clock pulses and having a reset terminal connected to the output terminal of the voltage comparator.

9. A pulse detector according to claim 8; wherein the successive groups of output detection signals comprise successive ones of the output detection signals.

* * * * *